(12) United States Patent
Hedberg et al.

(10) Patent No.: US 8,061,056 B2
(45) Date of Patent: Nov. 22, 2011

(54) APPARATUS AND METHOD FOR DRYING A SOLID OR LIQUID SAMPLE

(75) Inventors: Herbert J. Hedberg, N. Attleboro, MA (US); Brian Kangas, Millbury, MA (US)

(73) Assignee: Modular SFC, LLC, N. Attleboro, MA (US)

( * ) Notice: Subject to any disclaimer, the term of this patent is extended or adjusted under 35 U.S.C. 154(b) by 939 days.

(21) Appl. No.: 12/038,405

(22) Filed: Feb. 27, 2008

(65) Prior Publication Data

US 2009/0165326 A1 Jul. 2, 2009

Related U.S. Application Data

(60) Provisional application No. 60/009,816, filed on Jan. 2, 2008, provisional application No. 61/010,435, filed on Jan. 8, 2008, provisional application No. 61/010,670, filed on Jan. 10, 2008.

(51) Int. Cl.
*F26B 5/08* (2006.01)
(52) U.S. Cl. ............... 34/312; 34/381; 34/58; 34/90; 62/55.5; 118/52; 118/320; 427/240; 427/425
(58) Field of Classification Search ............... 34/312, 34/381, 58, 75, 90, 60, 413, 497, 87; 62/55.5; 118/52, 320; 427/240, 425
See application file for complete search history.

(56) References Cited

U.S. PATENT DOCUMENTS

| | | | | |
|---|---|---|---|---|
| 2,184,100 | A | | 12/1939 | Mondloch |
| 2,561,395 | A | * | 7/1951 | Marshall ............... 159/4.01 |
| 3,763,572 | A | * | 10/1973 | Titus ............... 34/58 |
| 4,297,792 | A | * | 11/1981 | Harter ............... 34/380 |
| 4,327,661 | A | | 5/1982 | Boeckel |
| 4,341,342 | A | | 7/1982 | Hara |
| 4,683,009 | A | | 7/1987 | Shriver |
| 5,334,130 | A | | 8/1994 | Glater et al. |
| 6,716,285 | B1 | * | 4/2004 | Weyburne et al. ......... 118/52 |
| 6,881,579 | B2 | * | 4/2005 | Hilson et al. ............ 436/47 |
| 7,610,780 | B2 | * | 11/2009 | Malaguti ............... 68/18 R |
| 2002/0090729 | A1 | * | 7/2002 | Neeper et al. ............ 436/45 |
| 2002/0090737 | A1 | * | 7/2002 | Levin et al. ............ 436/180 |
| 2004/0071595 | A1 | * | 4/2004 | Neeper et al. ............ 422/72 |
| 2009/0165326 | A1 | * | 7/2009 | Hedberg et al. .......... 34/312 |

(Continued)

FOREIGN PATENT DOCUMENTS

DE 38 17 962 A1 8/1989

(Continued)

OTHER PUBLICATIONS

"Notification of Transmittal of the International Search Report and the Written Opinion of the International Searching Authority, or the Declaration", mailed Jul. 24, 2009, International Application No. PCT/US2008/014079, 13 pages.

*Primary Examiner* — Stephen M. Gravini
(74) *Attorney, Agent, or Firm* — Cesari and McKenna, LLP (57) ABSTRACT

This disclosure describes a sample drying system and method that provides a high rates of evaporation and sublimation that is commonly employed in compound processing procedures. The drying increases the sample-solute concentration and removes the solvent completely to produce the dried sample as a non-volatile solute precipitate. Re-circulating of drying gas is disclosed along with a solvent cold trap.

32 Claims, 5 Drawing Sheets

U.S. PATENT DOCUMENTS

2009/0249801 A1* 10/2009 Hedberg ................. 62/55.5
2010/0101109 A1* 4/2010 Hedberg et al. ............. 34/487

FOREIGN PATENT DOCUMENTS

| | | |
|---|---|---|
| EP | 1 134 530 A | 9/2001 |
| EP | 1358928 A1 * | 11/2003 |
| GB | 1 037 856 A | 8/1966 |
| GB | 2 230 203 A | 10/1990 |
| GB | 2 259 756 A | 3/1993 |
| GB | 2 348 825 A | 10/2000 |
| WO | WO 02062456 A1 * | 8/2002 |
| WO | WO 2004/040214 A | 5/2004 |

* cited by examiner

APPARATUS AND METHOD FOR DRYING A SOLID OR LIQUID SAMPLE

RELATED APPLICATIONS

The present application claims the benefit and priority of the following commonly owned U.S. patent applications. A.) Centrifugal Fraction Collection System and Method, filed Sep. 19, 2007, Ser. No. 11/901,817. B.) U.S. Provisional Patent Applications, all entitled "Device and Method for Concentration of Solvents," application Nos. 61/009,816, filed Jan. 2, 2008; 61/010,435, filed Jan. 8, 2008; and 61/010,670, filed Jan. 10, 2008, respectively. These applications are hereby incorporated herein by reference.

BACKGROUND OF THE INVENTION

1. Field of the Invention

The present invention relates to the removal of solvents from a solution to produce non-volatile material or precipitates, and more particularly to provide high rates of evaporation and sublimation commonly applied in compound processing procedures to accelerate production of dry non-volatile materials.

2. Background Information

Compound processing to separate mixtures of chemical compounds into pure individual components usually includes a series of sequential dissolution process steps interspersed with drying steps. The drying step may only increase the concentration of a liquid or solid, but often complete drying of the non-volatile precipitates is needed before a re-dissolution is performed. To recover the dissolved non-volatile materials as dry powders or to increase the concentration of compounds, three approaches are used: a) vacuum centrifuges; b) freeze drying; and c) blow down concentrators. Multi-step compound processing is time consuming and expensive, and drying steps are in the critical path of any process because drying must be complete before the next step begins. Any reduction in drying time is advantageous.

Vacuum centrifuges combine a high performance vacuum pump to create very low pressure conditions inside the chamber of a centrifuge rotor to increase the rate at which solvent molecules can escape from the surface of a solution. The centrifugal force keeps solutions in their containers and prevents the violent boiling of the solution in the vacuum environment. A cold trap is usually configured to scavenge solvent molecules as they migrate from the higher concentration space inside the vacuum centrifuge to the low concentration space inside a solvent collection vessel in the cold trap. High performance vacuum systems are needed to speed drying, but such vacuum systems are expensive to buy and operate. However, these expensive, high performance systems working with water-containing solvent (which is the most commonly occurring solvent in biological samples) still only have the ability to remove water at about 0.5 mL/hr. It would be advantageous to increase the removal rate of water in such systems.

Freeze drying is a technique chosen typically when solute molecules are subject to degradation at temperatures above freezing or when in liquid solutions. This process requires that the solution be frozen initially. The container with the frozen solvent material is placed in the freeze drying apparatus. A hard vacuum is pulled on the surface of solid solution whereupon solvent molecules escape (sublime) from the solid solution. Since sublimation is endothermic it tends to maintain the solid frozen state of the solution. The now free solvent molecules migrate to and are collected in the lower concentration region of the cold trap solvent collection container. This approach retains the expensive vacuum system while adding, in some applications, expensive refrigeration equipment. If water is used as a solvent, the time to pre-freeze compound solutions adds to the time and effort to bring the compounds to dryness.

Blow-down concentrators create a continuous flow of a gas onto the surface of the liquid (or solid) solution. The gas flow promotes the escape of solvent molecules from the solution container so that they can be carried away in the flow of used gas out an exhaust port. The blow-down unit can be located inside a fume hood so that solvent vapors are not released to the workspace, or the exhaust port can be connected to a cold trap to capture the solvent molecules in a container. In every case, the exhaust outlet is directed to a fume hood. Blow-down concentrators are configured with specific gasses which are non-reactive to the solute compounds so that compound degradation does not occur. Nitrogen is commonly chosen to prevent degradation of potentially reactive compounds from oxygen in the air.

Blow down concentrators are not recommended for complete drying since the flow of drying gas will carry away the dry material. Using industry standard tube (test tube-like) tube containers, known blow down driers suggest a maximum of two (2) liters per minute of gas flow per solution tube container. Furthermore, it is suggested that the solution not be dried to a powder, but to a more concentrated liquid state, since this conservative gas flow rate may disturb a dry sample. The inability to dry completely a sample solution reduces the performance of blow down concentrators, and their consumption of gas (usually nitrogen) adds to the operating costs of blow down systems.

SUMMARY OF THE INVENTION

The present invention provides a centrifuge with sample solutions carried in tubes, and an ambient blow down gas filling the centrifuge cavity. The blow down gas is forced into each tube with a centrifugal fan, and emerges carrying along solvent molecules from the sample solute being dried. Herein, as would be understood by those skilled in the art, "sample" as sued herein defines a precipitate in a solution that is dried to remove the solvent leaving only the dried precipitate. Another centrifugal fan is arranged to carry the solvent and blow down gas away from the centrifuge cavity to a cold trap where the solvent collects and the blow down gas is retrieved for reentry into the centrifuge.

In this embodiment, the centrifugal force holds the sample intact in the tube container. The present invention allows a substantially higher velocity of blow down gas to be driven into the tube container. The effect is that the drying rate for the sample without the use of a vacuum may be five or more times higher than in known blow down driers. In addition, the centrifugal force maintains sample integrity to allow the present invention to dry the sample completely to a dry fine particulate powder.

In one illustrative embodiment, a fan blade structure is built onto the centrifuge rotor. The blades end at the openings of the tube containers. A cover is placed over the fan blades and a deflector portion of the cover re-directs the gas being driven by the fan blades into the tube containers. In one illustrative embodiment, the gas flow rate into any one tube container may be run upwards from 2 liters per minute and may reach 76 liters per minute (thirty eight time the prior art gas rate) or more.

In another illustrative embodiment, the blow down gas enters the centrifuge cavity via a venture-type tube arrangement, and in another application the drying gas enters into a plenum with feeder tubes that extend to the sample container openings. The drying gas is forced out the feeder tubes and into the sample containers as the rotating sample containers pass by.

It will be appreciated by those skilled in the art that although the following Detailed Description will proceed with reference being made to illustrative embodiments, the drawings, and methods of use, the present invention is not intended to be limited to these embodiments and methods of use. Rather, the present invention is of broad scope and is intended to be defined as only set forth in the accompanying claims.

BRIEF DESCRIPTION OF THE DRAWINGS

The invention description below refers to the accompanying drawings, of which.

Figure 1A:
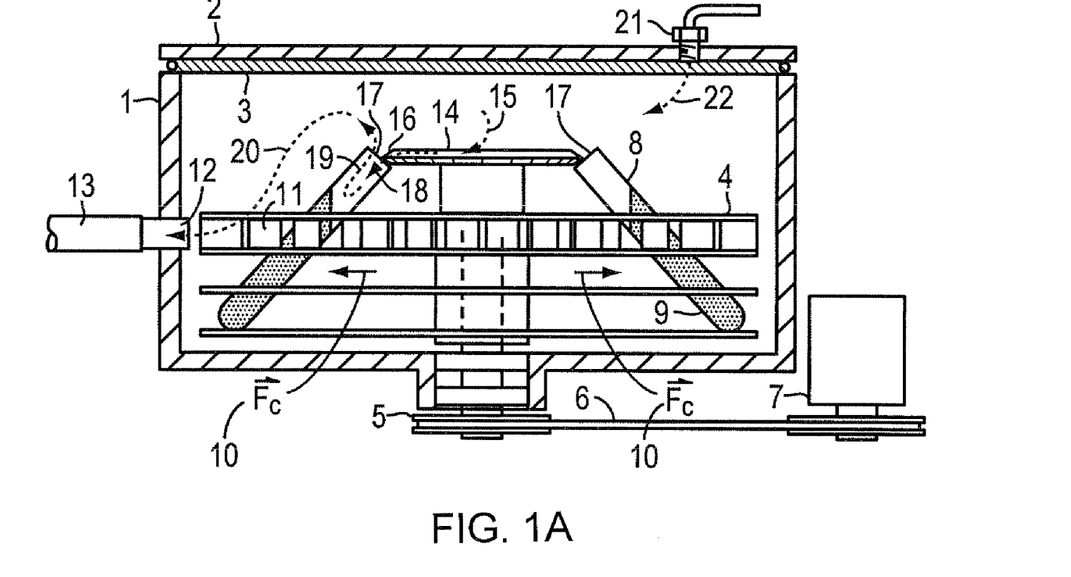
FIG. 1A is a cross section of centrifugal drying system with fan disk 14 attached to spinning centrifuge carrier 4 at height coincident with openings 17 of containers 8 holding samples 9 to be evaporated or sublimed.
Figure 1B:
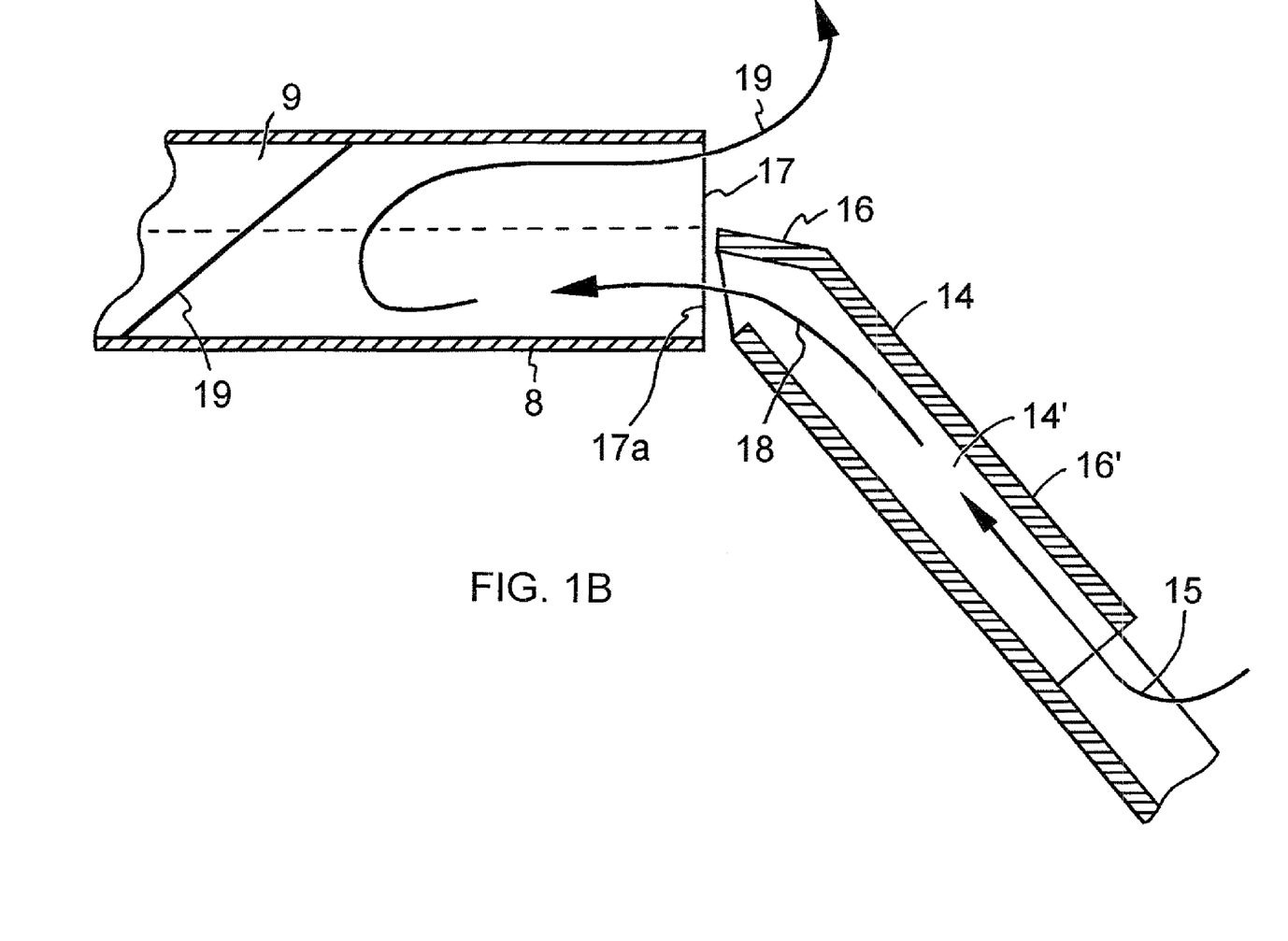
FIG. 1B is a detail drawing the blow down air flow into a tube container.
Figure 2:
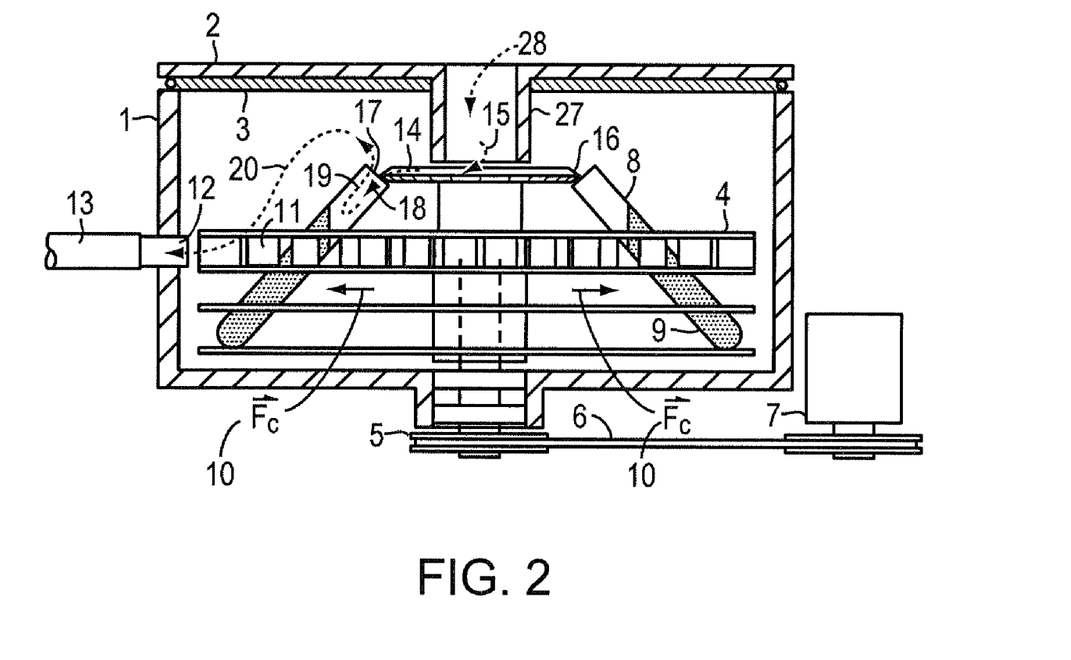
FIG. 2 is a system configured for maximum drying rate where relatively dry ambient air 28 is provided to the inlet of the centrifugal fan disk 14 through a venturi 27 with relatively low restriction to airflow in 28 or out 20.

FIG. 4 is a cross section of centrifugal fan disk 14 integrated with fraction distributor subsystem 23 of centrifugal fraction collector. Atomized eluant spray 25 encounters the centrifugal fan gas-flows 18 and 19 within the collection containers 8 promoting rapid dry powder formation 26 of any non-volatile material dissolved or precipitated within the eluant flow stream;

FIG. 5 is a concentrator device with two levels of containers 8 and two fans 14 driven by motor 38;

FIG. 6 is a sample concentration device where blow-down gas supply is provided by an external compressed gas supply attached to plenum 42 by fitting 41. Gas enters containers 8 as container openings 17 are swept past stationary nozzle array 43; and

FIG. 7 illustrates the application of the present invention to a microtiter plate application.

DETAILED DESCRIPTION OF AN ILLUSTRATIVE EMBODIMENT

FIG. 1A shows a cross section of a typical centrifugal vacuum concentrator where a spinning carrier 4 is contained within a closed environment comprising an enclosure housing 1 and a cover 2 between which is fitted a gasket 3 to prevent solvent vapors from escaping into the user workspace. Carrier 4 is rotated at moderate speed, for example 1,500 RPM, by spindle, bearing, and pulley assembly 5 driven by V-belt 6 which is powered by motor pulley assembly 7.

Collection tube containers 8 are filled with the mixture 9 to be dried and inserted into sample carrier 4. The centrifugal force generated by the spinning sample carrier 4 holds the sample material 9 within the tube containers. This force maintains sample integrity in fraction collector applications by maximizing the capture rate of non volatile sample materials. In this drying application the yield and purity of non-volatile sample materials is preserved by the centrifugal force despite the relatively violent flow of a turbulent drying gas which this invention introduces into the sample containers to sweep out volatile solvent molecules.

The sample carrier also includes a plurality of radially mounted impeller blades 14' to sweep gas and solvent molecules within the centrifuge housing 1 to the circumference of the spinning sample carrier. By providing fitting 12 and hose 13, the pressurized region gas and solvent molecules is vented out of the chamber. This reduces the concentration of vapor molecules in the drying gas and increases its ability to accept newly evaporated solvent molecules from within the sample containers by gas flows 18 and 19. Depending upon the configuration of the supply of dry gas to the containment space, the sample impeller blades 11 may also serve to reduce the local pressure at the sample surface, and similar to pulling a vacuum, facilitate the evaporation of sample solvents.

A second centrifugal planar disk fan 14, composed of radially mounted impeller blades, is fixed to the center axis of the centrifuge. The circumferential ends of the blades terminate at the openings 17 of the tube containers 8. See FIG. 1B, as the centrifuge spins, gas is drawn into the fan 14 at the center shown by the flow 15. The impeller blades 14'

The fan is 14, the fan blades 14.' force 18 the gas to the perimeter of the blades where a top surface 16' is bent downwards 16 to divert the horizontal flow of gas into lower half 17*a* of the tube container 8. This cover 16' may rest on the impeller blade 14' as they do not move with respect to each other, and this cover 16' may only cover the distal ends of the impeller blades leaving an entrance opening at the center axis of the fan 14. The gas flow 18 circulates within the containers 8 across the surface 19 of sample solutions 9 sweeping volatile solvent molecules out of the tube container 8 along with the blow down gas along the flow-path 19. These freed solvent molecules are then caught up in containment exhaust gas-flow 20 and ejected from the containment housing 1. As mentioned above the blow down gas flow rate may far exceed that found in prior art systems because centrifugal force from the spinning sample carrier is maintaining sample integrity.

Although the fan is described above as including "impeller blades," the mechanism that drives the blow down gas into the tube containers holding the sample to be dried, may be described as walls, tubular structures, etc. that may be made of any acceptable material known to those skilled in the art for given applications. Moreover, the shape of the "impeller blades" as they traverse outwardly to the tubular containers may be of various shapes, the flow path ways not be straight, they may curve and/or be of unequal cross sections, etc.

Users of sample concentration equipment frequently have concerns that the extended exposure of certain unknown (or known) solute molecules to reactive evaporative gasses (such as oxygen) will cause undesired chemical changes (degradation) of the sample material being dried. To concentrate samples 9 in a particular environment, the specific desired gas is introduced into the housing via a gas fitting 21 allow a gas-flow 22. Because no other make-up gas is available, the volume of gas exiting the housing by fitting 12 and hose 13 is necessarily equal to the volume gas introduced through fitting 21. In practice the blow down gas may be retained in the housing and recirculated multiple times to reduce the amount of desired gas which is consumed. Consequently, better economy and/or productivity can be obtained by balancing the consumption of dry make-up gas with the speed of evaporation.

Use of the centrifugal fan 14 to dry sample solutions 9 provides drying rates which compare favorably to those obtained from traditional vacuum-centrifuge drying systems. In this instance the complex, expensive, and maintenance-prone vacuum pump is replaced by a single centrifugal fan assembly 14 with no moving parts. In addition, the elimination of the vacuum pump from traditional evaporator systems may save about $3,000 in the cost of the pump for each system and about 10 KWH to 20 KWH of electricity to dry each batch of sample containers 8.

Another illustrative embodiment is shown in FIG. 2, where the cover 2 has been fitted with a central venturi 27 which extends downward to a point just above the top surface of the centrifugal fan 14. It's inside diameter is similar to that of the inlet hole in the top surface of the centrifugal fan 14. With this configuration, ambient gas 28 is drawn into the venturi 27 by the vacuum resulting at 15 from the action of the spinning impeller blades of fan 14. If this gas is relatively de-humidified, its ability to capture solvent molecules from the surface of samples 9 by gas-flows at 18 and 19 will be significantly enhanced.

A key contribution that the venturi-type port 27 makes to the drying rate is from the introduction of drying gas with a low volatile solvent molecule content. The venturi also helps maximize the rate of drying by preventing the induction of vapor-laden gas already in the housing back through the centrifugal fan 14 a second time instead of being exhausted out of the housing through fitting 12 and hose 13.

Experimentation has demonstrated that the rate of evaporation of solution 9 is proportional to the velocity of gas-flow across the surface at 18 and 19. By partially or completely blocking the flow passages through the centrifugal fan 14 or allowing dry gas leakage from the fan before entering the tubular container, the rate of evaporation can be controlled. For example a reduction by as much as 50% has been achieved. This means of flexibility of modulating the airflows 18 and 19 to achieve a specific drying rate may be advantageous to solvent drying practioners.

Figure 3:
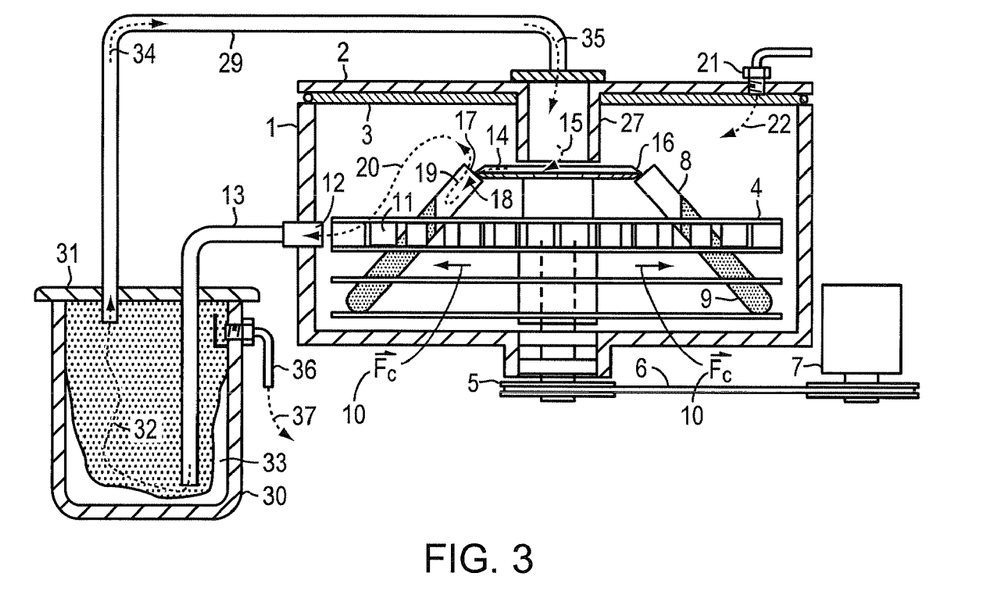
FIG. 3 shows a cold trap 30 has been included in a recirculation path comprised of outlet hose 13 and inlet hose 29 to condense solvent molecules travelling with the gas molecules around the closed-loop system during the drying process;

In most laboratory operations today, recovery of volatile solvents from concentration activities is mandatory. In larger facilities, the volume of waste solvent is compared to the volume of solutions subjected to various drying processes to assure that recovery processes are effective and being utilized. FIG. 3 illustrates the present invention with a cold trap 30 and cover 31. The cold trap condenses the volatile solvent molecules which have been picked up by circulating gas from the drying solutions 9. The efficiency of the concentration process depends largely on a sufficiently low temperature at the interior walls of the cold trap to freeze the solvent molecules 33 and a sufficiently large cold trap volume to assure adequate residence time of the vapor-laden circulating gas within the cold trap so that the condensation can occur. Dried gas within the cold trap travels back to the centrifugal fan by flow-paths 32, 34, and 35 by connecting hose 29.

If the user desires a specific gas environment during the drying process, this gas is introduced to the system at fitting 21 resulting in gas-flow 22. Because this is necessarily a closed system to prevent the escape of solvent molecules from solutions 9, a vent fitting 36 is provided behind a baffle in the cold trap 30. The rate of make-up gas-flow 22 will create an equal rate of vent gas-flow 37. Because gas-flow 37 could still contain some uncondensed solvent molecules not captured in the frozen material at 33, a hose should be connected between vent fitting 36 and a convenient chemical fume hood facility (not shown). A charcoal filter or other solvent scrubber may be inserted between the vent and fume hood.

With respect to FIG. 3 the drying performance can be increased by the judicial application of heat to the drying process. Some compounds are too unstable to survive the application of any heat so consideration must be made for the materials involved.

Irradiating the enclosed housing volume with infrared light energy to warm the samples is a common strategy familiar to those skilled in the art. Using radiation to transfer heat to the samples is practical and necessary because of the prior art vacuum environment which exists within typical centrifugal concentrator systems. Heat transfer by convection is not possible in the vacuum. Heating by conduction is also employed in some higher end systems, however getting the necessary electrical power across a rotating interface to power heaters mounted in the rotor can be problematic.

Because the inventive system in FIG. 3 does not require vacuum to migrate solvent molecules, convection can be used to transfer heat to the drying samples. For example, a heating element 60 could be attached to the housing 1 to allow heat transfer from the interior walls of housing 1 to the sample liquid 9 inside the tube containers 8 by means of convection. Another location to add heat to the process would be to insert a heat exchanger 62 in series with hose 29 to warm the gas at 34 and 35 before it reenters the centrifugal fan 14.

As a practical illustration of the effectiveness of drying samples in a non-vacuum environment, consider the negative effect the prior art sample-cooling process of evaporation where sample solutions 9 freeze in their containers 8 predicated by high vacuum, which greatly reduces the rate of evaporation. Using the non-vacuum device described in this disclosure at drying rates up to 5-times that of typical vacuum drying equipment, no cooling of samples was detected because the interior of the housing is at atmospheric pressure; full of gas molecules at room temperature able to replace the thermal energy lost in the sample solutions due to evaporation. In a comparative test of a known vacuum system at 25 C the drying rate of water was about 0.5 mL/hour, while the drying rate of the present invention of FIG. 3 was 2.5 mL/hour. The drying rate is five times (×5) that of a prior art vacuum system resulting in five times less time to dry samples between processing steps.

Figure 4:
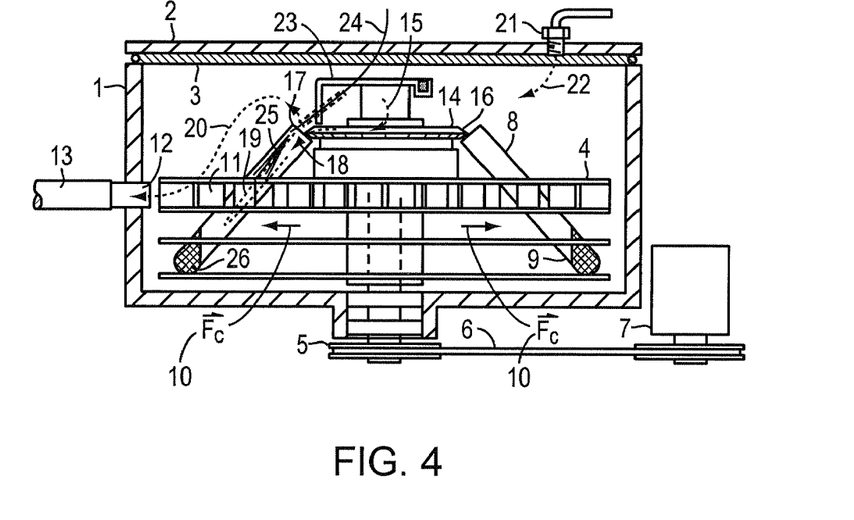
Figure 5:
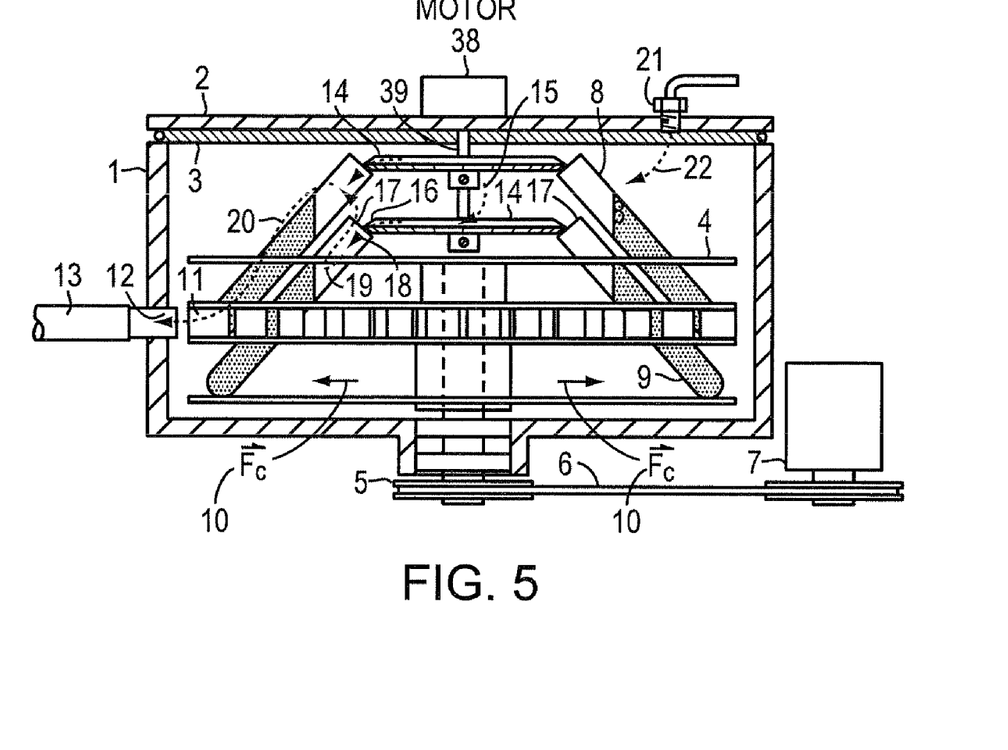
Figure 6:
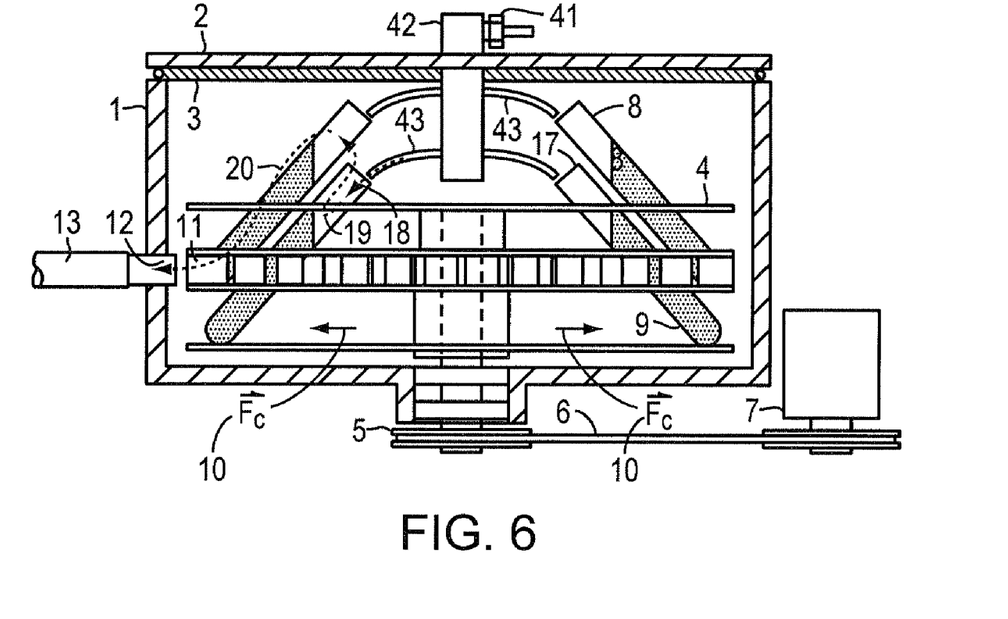
Figure 7:
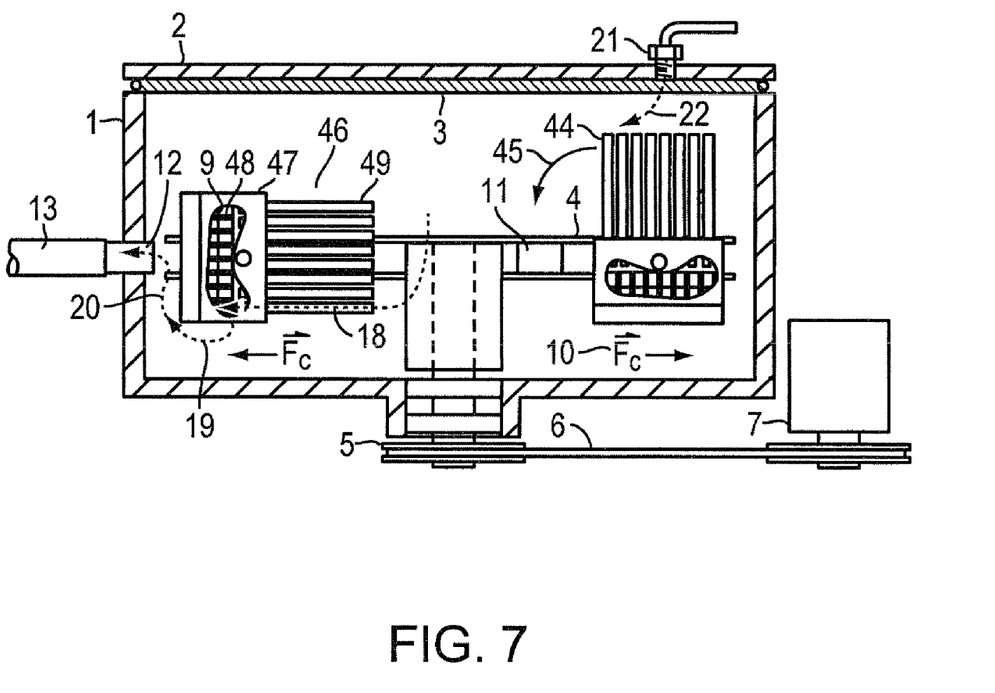

FIG. 4 of this disclosure shows centrifugal fraction collection system having centrifugal fan 14 to dry samples integrated into fraction distributor subsystem 23. The Centrifugal Fraction Collection System and Method shown in FIG. 4 is described and incorporated by reference in Patent Application filed Sep. 19, 2007, Ser. No. 11/901,817 and in incorporated by reference Provisional Patent Application filed Jan. 9, 2006, Ser. No. 60/879,385.

In this instance, the purpose is to collect and retain with high yield the non-volatile components of the sprayed sample material 25 from system eluant tube 24 while the carrier 4 is spinning, for example, at 1,500 RPM. Because the atomized volatile and non-volatile sample material 25 encounters the moving gas-flows 18 and 19 within container 8, the greatly increased solution surface area provides almost instantaneous drying of the non-volatile sample material which typically results in collection of very fine solid sample particles 26.

As before, the centrifugal force 10 captures the dense non-volatile components of the eluant spray 25 within the fraction containers 8. The less dense volatile components are forced from the container opening 17 and ejected from the containment housing 1 through port 12 and hose 13. Hose 13 is typically connected first to a cold trap (shown as 30 in FIG. 3) which, through condensation of volatile gas molecules in the ejected gas-flow, scrubs from the gas-flow stream all volatile solvent material which might otherwise be released to the environment.

The integration of the centrifugal fan 14 to convert collected eluant spray 25 into dry solute material 26 provides the potential for significant reductions in sample preparation time and increased fraction integrity and yield. Typically, fraction solutions are collected in an operation separate and distinct from fraction drying. The present disclosure presents a device and method which combines the two operations into one that provides the benefit of reduced total processing time and reduced operator handling of samples.

The blow-down gas 18 may be selected from any suitable source given the application. The purpose of the centrifugal force in this invention is to capture and maintain the integrity of the samples in the containers being dried. If this force is sufficiently high, for example that generated by 1,500 RPM, then non-volatile sample material will remain captured in the bottom of the sample containers nearly regardless of the flow rate of blow-down gas injected into the sample containers.

FIG. 5 shows a dryer configuration where two fans (both 14), an upper and a lower, are fixed to a shaft 39 from a motor 38 mounted to the cover of the enclosure. It is common practice to configure sample containers in multiple tiers to maximize the productivity of a given concentrator device. In FIG. 5 the second fan 14 provides a stream of blow-down gas to the second level of sample container openings 17.

Disconnecting the centrifugal fan 14 from the spinning sample carrier potentially allows running the fan 14 at speeds significantly higher than the sample carrier 4. Optimum fan RPM to produce the most effective gas flow rate might be significantly different from that desirable to achieve the centrifugal force required to maintain sample integrity. Changing the relative speeds of the centrifuge compared to the sample carrier is well within the skill of those skilled in the art.

An alternative means to provide blow-down gas to all containers is from an external source of compressed gas as shown in FIG. 6. The user selects the gas compound and flow rate suitable for the particular application. The external gas supply (not shown) is connected to plenum 42 at fitting 41. The gas pressurizes the interior of plenum 42 and exits out at least one nozzle 43. The vertical height of the nozzle 43 outlet is directed off-center from the container openings 17. In this way, as a container 8 sweeps past a nozzle 42 the gas flow enters the tube by a flow path 18 and exits the container 8 by a flow path 19 after sweeping escaped molecules from the surface of the sample 9. FIG. 6 shows this external gas supply implementation with two tiers of sample containers 8 as discussed previously. Consequently, two tiers of nozzles 43 are also required.

FIG. 7 illustrates a drying configuration for microtiter plates 48. These container array devices are familiar to those skilled in the art and may house ninety six sample cavities, each with a volume of 2.2 milliliters, for example. Because a fixed 45° angle in the rotor would prevent the utilization of a third of the cavity volume, these container arrays are frequently centrifuged by placing the plates in a swinging bucket 47 sitting in a horizontal position (side 44). When the spinning carrier 4 increases in RPM, the buckets 47 swing outwards in a motion shown by arrow 45. Spinning at full speed, the bucket 47 and plate 48 will assume a vertical orientation like that shown (side 46). A blow-down gas to the sample cavities is located in an array of tubes 49 just above the cavity openings and coincident with each of the openings. In this way, blow-down gas flow 18 will be produced by each of the tubes in array 49 such that the flow reaches the surface of the sample 9 in the cavity. As before, exiting gas flow 19 is collected by centrifugal fan blades 11 and exhausted from housing by flow 20 through fitting 12 and hose 13.

It should be understood that above-described embodiments are being presented herein as examples and that many variations and alternatives thereof are possible. Accordingly, the present invention should be viewed broadly as being defined only as set forth in the hereinafter appended claims.

What is claimed is:

1. A sample drying system comprising:

a centrifuge defining a central axis about which the sample carrier rotates;

at lest one sample container, holding a sample to be dried, positioned radially with respect to the central axis, wherein the sample container defines an opening substantially facing the central axis;

a drying gas, a flow pathway for the drying gas wherein the flow pathway includes an opening proximate the central axis and an exit adjacent to the at least one sample container opening; wherein when the sample carrier is rotating, the drying gas enters the flow pathway opening and is driven radially along the flow pathway to the opening of the at least one sample container; wherein the drying gas is driven to the sample to be dried; wherein the drying gas picks up volatile solvent molecules and carries them out of the sample container.

2. The sample drying system of claim 1 wherein the flow pathway comprises a fan and a drive system, wherein the rotating speed of the fan may be made different from the rotating speed of the centrifuge.

3. The sample drying system of claim 1 further comprising a deflection panel located at the exit of the flow pathway, wherein the deflection panel directs the drying gas into the sample container using about one half of the sample container opening.

4. The sample drying system of claim 1 further comprising a controlled blockage in the flow pathway wherein the volume of drying gas entering the at least one sample container is correspondingly controlled.

5. The sample drying system of claim 1 further comprising controlled leakage openings along the flow pathway wherein the volume of drying gas entering the at least one sample container is correspondingly controlled.

6. The sample drying system of claim 1 further comprising an entrance port through which drying gas is introduced into the centrifuge system, and an exit port through which the drying gas and volatile solvent molecules exit the centrifuge.

7. The sample drying system of claim 6 wherein the volume of drying gas entering the system is controlled to reduce drying gas consumption with respect to the volume of drying gas and volatile solvent molecules exiting the system, wherein the drying gas consumption is balanced with the drying time of the sample.

8. The sample drying system of claim 5 further comprising a cold trap, wherein the drying gas and volatile molecules exit the sample drying system and enter the cold trap, wherein the volatile molecules condense within the cold trap and the drying gas is returned to the entrance port.

9. The sample drying system of claim 5 wherein the entrance port comprises a venturi-style port centered such that the blow down gas enters along the central axis.

10. The sample drying system of claim 1 further comprising a plurality of sample containers distributed radially around the central axis, the plurality defining generally a first disk shaped plane about the central axis.

11. The sample drying system of claim 10 further comprising at least a second plurality of sample containers distributed radially around the central axis, the at second plurality of sample containers defining at least a second disk shaped plane about the central axis, wherein the at least a second disk shaped plane is offset axially with respect to the first disk shaped plane, and wherein there is a flow pathway to the opening of the second plurality of sample containers.

12. The sample drying system of claim 1 wherein the at least one sample container is a tube with an opening at one end, and wherein the drying gas flow rate into the tube container is greater than 2.0 liters per minute.

13. The sample drying system of claim 12 wherein the flow rate of the drying gas sweeps out volatile solvents but the centrifugal force of the rotating sample carrier maintains sample yield and purity.

14. The sample drying system of claim 12 wherein the drying gas flow rate into the tube container is between about 2.0 and about 76 liters per minute.

15. The drying system of claim 1 wherein the at least one sample container is a microtiter plate.

16. The drying system of claim 1 further comprising a second fan arranged to drive the drying gas and volatile molecules within the sample drying system out through an exit port.

17. A sample drying system comprising:
a centrifuge defining a central axis about which the sample carrier rotates;
at least one sample container, holding a sample to be dried, positioned radially with respect to the central axis, wherein the at least one sample container defines an opening substantially facing the central axis;
a drying gas;
at least one tube section defining a flow pathways extending from an entrance port to the at least one sample container opening, the flow pathways not rotating with the sample carrier, wherein the drying gas is driven through the flow paths and into the at least one sample container, as it travels by with the rotating sample carrier, where the drying gas picks up solvent molecules and carries them out of the at least one sample container.

18. The drying system of claim 17 further comprising a plenum with an entrance port allowing the drying gas to enter the plenum, wherein the plenum is positioned about along the axis of the centrifuge, and wherein the at least one tube section extends from the plenum to the at least one sample container opening.

19. A method for drying samples, the method comprising the steps of:
rotating at least one sample container around a central axis, the at least one sample container having an opening,
positioning the at least sample container substantially radially, wherein when the sample carrier is rotating the at least one sample container, the opening substantially faces the central axis;
flowing a drying gas along a flow pathway to the at least one sample container opening;
flowing the drying gas to the sample to be dried; wherein the drying gas picks up volatile solvent molecules and carries them out of the sample container.

20. The method of claim 19 further comprising the step of controlling the volume of drying gas flowing into the at least one sample container.

21. The method of claim 19 further comprising the step of deflecting the drying gas with a deflection panel located at the exit of the flow pathway, wherein the drying gas enters the at least one sample container using about one half of the sample container opening.

22. The method of claim 19 wherein the sample container is a tube and the step of flowing the drying gas comprises the step of flowing the drying gas at a rate greater than 2 liters per minute into the tube container.

23. The method of claim 19 wherein the sample container is a microtiter plate.

24. The method of claim 19 further comprising the steps of introducing the drying gas via an entrance port, and exiting the drying gas and volatile solvent molecules via an exit port.

25. The method of claim 24 further comprising the steps of:
controlling the volume of drying gas entering the system with respect to the volume of drying gas and volatile solvent molecules exiting the system, and
balancing the consumption of drying gas used with the drying time of the sample.

26. The method of claim 24 further comprising the steps of:
introducing the drying gas and volatile molecules into a cold trap;
condensing the volatile molecules within the cold trap; and
recirculating the drying gas back to the sample drying system.

27. The method of claim 24 wherein the step of introducing the drying gas comprises the step of introducing the drying gas via a venturi-type port.

28. The method of claim 19 further comprising the step of rotating a plurality of sample containers distributed radially around the central axis, the plurality of sample containers defining generally a first disk shaped plane about the central axis, and wherein there are a plurality of flow pathways to the openings of the first plurality of sample containers.

29. The method of claim 28 further comprising the step of rotating at least a second plurality of sample containers distributed radially around the central axis, the at least second plurality of sample containers defining at least a second disk shaped plane about the central axis, wherein the at least a second disk shaped plane is offset axially with respect to the first disk shaped plane, and wherein there are a plurality of flow pathways to the openings of the second plurality of sample containers.

30. A method for drying a sample, the method comprising the steps of:
rotating a sample carrier around a central axis,
holding a sample to be dried in at least one sample container that has an opening;
radially positioning, with respect to the central axis, the at least one sample container with the opening substantially facing the central axis;
introducing a drying gas into a plenum, wherein the plenum is positioned about along the central axis of the centrifuge;
the drying gas exiting the plenum via flow pathways extending from the plenum to the at least one sample container opening, the flow pathways not rotating with the centrifuge, wherein the drying gas is driven through the flow paths and into the at least one sample container, as it travels by with the rotating sample carrier, and
the drying gas picking up solvent molecules and carrying them out of the at least one sample container.

31. The method of claim 30 further comprising the step of condensing the volatile molecules in a cold trap and recirculating the drying gas back into the plenum.

32. The method of claim 30 wherein the steps of introducing a drying gas into a plenum and exiting the plenum is replaced by a step of introducing a drying gas into a proximate end of a tube section and delivering the drying gas from the distal end to the tube into the at least one sample container.

* * * * *

UNITED STATES PATENT AND TRADEMARK OFFICE
CERTIFICATE OF CORRECTION

PATENT NO. : 8,061,056 B2  
APPLICATION NO. : 12/038405  
DATED : November 22, 2011  
INVENTOR(S) : Herbert J. Hedberg et al.

Page 1 of 1

It is certified that error appears in the above-identified patent and that said Letters Patent is hereby corrected as shown below:

On Patent Page 1, please correct as follows:

Related U.S. Application Data (60) Provisional application No. ~~60/009,816~~ 61/009,816, filed on Jan. 2, 2009, provisional application No. 61/010,435, filed on Jan. 8, 2008, provisional application No. 61/010,670, filed Jan. 10, 2008.

In Patent Col. 5, line 36, please correct as follows:

geous to solvent drying ~~practioners~~ practitioners.

Signed and Sealed this  
Twenty-fourth Day of January, 2012

David J. Kappos  
*Director of the United States Patent and Trademark Office*